United States Patent [19]
Palumbo et al.

[11] Patent Number: 6,149,640
[45] Date of Patent: Nov. 21, 2000

[54] PLASTIC TAPES HAVING ROUNDED CROSS SECTION AND METHODS FOR MAKING SUCH TAPES

[75] Inventors: Gianfranco Palumbo, Bad Homburg, Germany; Italo Corzani, Chieti, Italy

[73] Assignee: The Procter & Gamble Company, Cincinnati, Ohio

[21] Appl. No.: 09/011,236

[22] PCT Filed: Aug. 13, 1996

[86] PCT No.: PCT/US96/13144

§ 371 Date: Feb. 3, 1998

§ 102(e) Date: Feb. 3, 1998

[87] PCT Pub. No.: WO97/06764

PCT Pub. Date: Feb. 27, 1997

[30] Foreign Application Priority Data

Aug. 14, 1995 [EP] European Pat. Off. .............. 95830364

[51] Int. Cl.[7] .......................... A61F 13/15; B32B 15/04; B32B 7/12

[52] U.S. Cl. .......................... 604/389; 428/343; 428/220; 264/296

[58] Field of Search .................................... 604/386, 389, 604/390; 428/343, 220; 269/296, 161, 345, 138, 349

[56] References Cited

U.S. PATENT DOCUMENTS

| 3,193,034 | 7/1965 | Pandolfo | 428/343 |
| 3,931,666 | 1/1976 | Karami | 604/389 |
| 4,237,889 | 12/1980 | Gobran | 604/389 |
| 5,133,706 | 7/1992 | Dixon | 604/389 |
| 5,312,387 | 5/1994 | Rossini et al. | 604/391 |
| 5,603,708 | 2/1997 | Seth | 604/391 |

*Primary Examiner*—Mark O. Polutta
*Attorney, Agent, or Firm*—Michael S. Kolodesh; David M. Weirich; Steven W. Miller

[57] ABSTRACT

Disclosed are flexible plastic tapes each having at least one rounded edge, a method for forming the rounded edge by the application of heat, and an absorbent article provided with such tapes. The edges are rounded to reduce their sharpness in order to reduce the risk of irritation or injury to a wearer of the absorbent article and/or to any person coming into contact with the tapes. The tapes have a thickness not greater than that at which the edge would be sharp if it were not rounded. The tapes are relatively stiff and formed from a plastic material such as polypropylene or polypropylene copolymer.

20 Claims, 1 Drawing Sheet

PLASTIC TAPES HAVING ROUNDED CROSS SECTION AND METHODS FOR MAKING SUCH TAPES

FIELD OF THE INVENTION

This invention relates to flexible plastics tapes, and to sanitary articles provided with such tapes. In particular the invention relates to diapers provided with such tapes.

BACKGROUND OF THE INVENTION

It is conventional to use flexible plastics tapes for holding a diaper in place. This is so with diapers for infants, though such tapes are also used for adult diapers. In its unused condition the diaper has a pair of tapes, one on each side, the tapes being secured to the rest of the diaper by, for example, heat sealing. The tapes have free end portions which are coated with adhesive, the adhesive surface each being covered prior to use with a backing film. At the time of use, the backing films are removed and the tapes adhered to the portion of the diaper which is then adjacent to them, the tape connections then being located adjacent either side of the waist of the infant or other user.

In order to provide adequate strength for the tapes, it is normal to use a strong, relatively stiff plastics material, such as polypropylene, in the form of solid tapes produced, for example, by extrusion. The term "solid" here is used to mean that the material of the tape is present throughout its cross-section, as opposed, for example, to tapes formed of matted fibres. The tapes are cut with a blade from a roll of material. Normally what is done is to start with a roll whose width is equal to the desired length of the tapes, and cut it into lengths equal to the desired tape width. However, the tapes are quite thin. They might be as much as 500 $\mu$m in thickness, but would normally be less than 200 $\mu$m, and typically about 100 $\mu$m or 150 $\mu$m. They might be as little as 20 or 25 $\mu$m in thickness. These values exclude the adhesive coating. As a result of their thinness the edges of the polypropylene tape are very sharp. The phenomenon is akin to that encountered with paper. There is therefore a risk of the person putting the diaper on the infant being cut by the tapes. Furthermore, it is found that movement by the infant after the diaper is put on can result in the tapes coming into contact with the infant's skin, which can be the cause of the irritation.

The problem is one which is known in the art, but the only solution proposed hitherto, as far as the present applicants are aware, is that described in EP-A-379850, which involves cutting the initial plastic material in a wave shape. This requires a specially constructed, and somewhat complex, cutting apparatus.

It is an object of the present invention to provide tapes in which the above problem is avoided or mitigated in a simple and effective manner, and a sanitary article, for example a diaper, using such tapes.

SUMMARY OF THE INVENTION

According to the present invention there is provided a flexible plastics tape formed using a plastics material, wherein at least one edge of the tape is rounded as viewed in cross-section and wherein the tape has a thickness not greater than that at which the said edge would be sharp if it were not rounded. In a preferred version the edges of the tape which have been cut are rounded.

The tape typically has a thickness of less than 500 $\mu$m, more typically less than 200 $\mu$m, still more typically less than 150 $\mu$m, and most typically of the order of 100 $\mu$m.

The invention further provides a sanitary article, for example a diaper, which comprises a fluid-absorbing body portion and at least one tape as just defined.

DETAILED DESCRIPTION OF THE INVENTION

Figure 1:
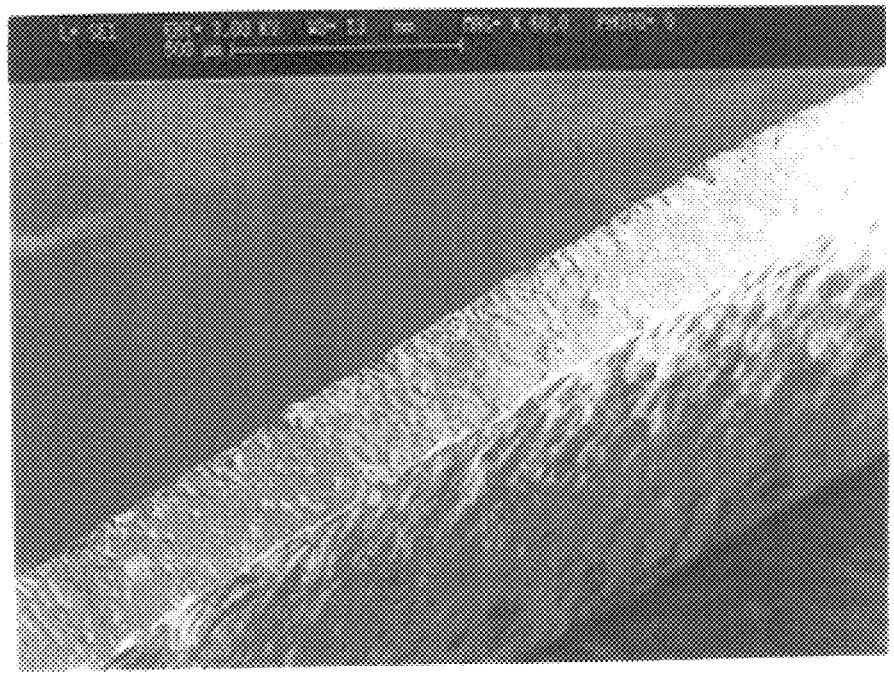
FIG. 1 shows the edge of a polypropylene plastic film, of a type conventionally used for diapers, before treatment with hot air at 350 deg. C.

The invention will now be described in more detail.

During diaper assembling, closure tapes are cut from a roll by a cutting device, and conveyed to a point at which they are fixed in place on the diaper. According to the present invention, at least one edge, and preferably both edges of the tapes have their sharpness reduced. One way of doing this is to arrange for the tapes to contact hot metallic surfaces during the above mentioned conveying process, so that they are softened or partially melted and thereby assume a curved shape as viewed in cross-section. Alternatively, and this is preferred, the hot metallic surfaces are formed by the cutting device itself, which is kept at the desired elevated temperature.

One point to note is that where rounding is achieved by contact with a hot surface, the plastics material of the tape must have a sufficiently low elongational viscosity to avoid the occurrence of lagging, a phenomenon in which the hot surface pulls filaments of material outwardly thereof and gives rise to an irregular surface. A low viscosity, and/or the maintenance of the material at a sufficiently high temperature for a sufficient length of time, also assists in ensuring that surface tension effects are able to produce the desired rounding of the edge.

Still more preferably, however, the rounding of the edges is achieved by directing hot air at the edges of the tape. For example, it has been found that air at 350° C. will produce the desired effect on a conventional polypropylene tape of a type normally used on diapers.

In general it is desirable that only a very small portion of the tape should be modified by heat in that way, e.g. a region up to 0.5 mm from the edge of the tape, whose overall width is in the region of 30 mm. This is desirable both for aesthetic reasons, and to avoid adversely affecting the functional characteristics of the main part of the tape.

Where rounding is achieved by contact with a hot surface, the temperature of the hot surface with which the tape is contacted can be different depending on the polymer nature and structure, on the crystallinity fraction and on the process speed and so on the time of contact. Similar considerations apply where hot air is used to achieve rounding.

In the case of highly crystalline polymers, for example homopolymer polypropylene, it is useful to work in a range between 20° C. below and 50° C. above its crystalline melting point.

In the case of polymers with lower crystallinity (e.g. propylene/ethylene copolymers) it is more meaningful to refer to the softening point of the polymer (e.g. determined by the ring and ball method according to ASTM E28-67) and work in a similar range around it.

In a preferred embodiment the tape material is a polypropylene copolymer containing up to 10% of ethylene. This makes the material intrinsically softer, which itself helps in partially reducing the sharpness of the edges. Moreover this lowers the softening point and makes easier the application of the present invention. In a more preferred embodiment this copolymer is a random copolymer. These materials have a limited heat-shrinkability which helps the curving of edges without giving macroscopic distortion to the tape, helping the formation of rounded edges also in the zones which do not reach a level of temperature sufficient for softening or melting. For example, MOPLEN EP2 C3OF is a random polypropylene copolymer containing 2% by weight of ethylene, and is available from HIMONT. At 100° C. it shrinks about 3%. Depending on the tape structure and process conditions, this level of shrinkage can be useful in the present invention.

In any case the degree of heat-shrinkage can be tailored to the desired level by properly formulating the polymer. For example, by blending the above mentioned polypropylene with the compatible hydrogenated hydrocarbon resin ARKON P-125 available from ARAKAWA CO., it is possible to modify the behaviour as follows:

| % of resin in PP | % of heat-shrinkage at 100° C. |
| --- | --- |
| 0% | 3% |
| 5% | 7% |
| 10% | 16% |
| 20% | 31% |
| 30% | 44% |

In this way it is possible to choose the optimum level of heat shrinkability useful in the particular application or process concerned.

However, the invention can also be applied even where the plastics material has not significant heat shrinkability. In that case, however, the temperature at which the edges are treated needs to be sufficient to cause melting of the material, thus permitting surface tension to cause the necessary rounding.

Figure 2:
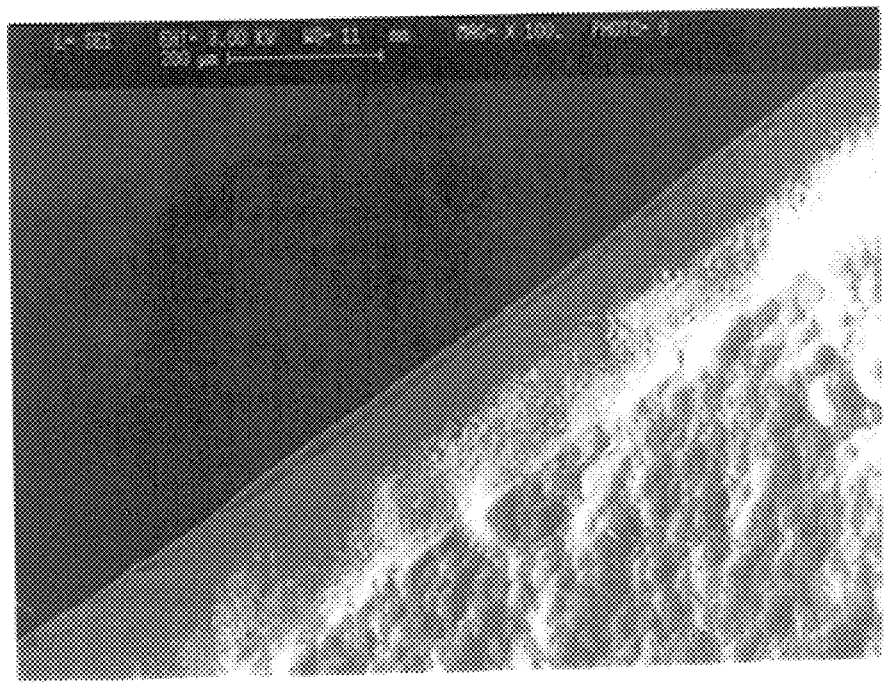
FIG. 2 shows the film from FIG. 1 after treatment with a hot air at 350 deg. C.

The invention is further illustrated in FIGS. 1 and 2 of the accompanying drawings. These are photomicrographs showing the edge of a polypropylene plastics film, of a type conventionally used for diapers, respectively before and after treatment with hot air at 350° C. The film on which the treatment was carried out was coated on the side facing away from view with a layer of adhesive. In FIG. 2 the layer can be seen quite clearly. In FIG. 1 a broken line has been added to mark the boundary between the adhesive and the plastics material. Comparison of the two Figures clearly shows the rounding which is achieved. It is also noteworthy that it is found that the process does not adversely affect the adhesive.

What is claimed is:

1. A flexible plastic tape having an adhesive coating covering at least a portion of the tape, the tape being formed using a plastic material, the tape having at least one edge, wherein the edge is rounded as viewed in a cross-section taken through the edge and wherein the tape has a thickness not greater than that at which the edge would be sharp if it were not rounded.

2. The tape according to claim 1, wherein the thickness thereof is less than 500 μm.

3. The tape according to claim 2, wherein the thickness thereof is less than 200 μm.

4. The tape according to claim 3, wherein the thickness thereof is less than 150 μm.

5. The tape according to claim 1, wherein the thickness thereof is of the order of 100 μm.

6. The tape according to claim 1, which has an adhesive coating thereon.

7. The tape according to claim 1, wherein both edges which have been cut are rounded as aforesaid.

8. The tape according to claim 1, wherein the plastic material essentially consists of polypropylene.

9. The tape according to claim 1, wherein the plastic material essentially consists of a copolymer of propylene and a further material the inclusion of which increases the softness of the tape.

10. The tape according to claim 9, wherein the plastic material is a propylene/ethylene copolymer.

11. The tape according to claim 10, wherein the plastic material comprises up to 10% by weight of ethylene.

12. The tape according to claim 11, wherein the copolymer is a random copolymer.

13. An absorbent article which comprises a fluid-absorbing body portion and at least one tape as claimed in claim 1, for securing the article in place on a user.

14. The absorbent article according to claim 13, wherein the article is a diaper.

15. The article according to claim 14, wherein a pair of the tapes is provided.

16. A method of rounding at least one edge of a flexible tape having an adhesive coating covering at least a portion of the tape, the tape being formed using a plastic material, the tape having at least one edge, wherein the edge is rounded as viewed in a cross-section taken through the edge and wherein the tape has a thickness not greater than that at which the edge would be sharp if it were not rounded, the method comprising the step of applying heat to the tape edge to be rounded.

17. The method according to claim 16, wherein heat is applied by contacting the edge to be rounded with a heated surface.

18. The method according to claim 16, wherein the edge is formed in a rounded condition by cutting the tape from a sheet of the plastic material using a heated cutter.

19. The method according to claim 16, wherein heat is applied by directing hot air at the edge to be rounded.

20. The method according to claim 19, wherein the tape edge to be rounded is subjected to a temperature which lies in a range from 20° C. below to 50° C. above the crystalline melting point of the plastic material, where the plastic material is highly crystalline, or the softening point of the plastic material, where the plastic material is not highly crystalline.

* * * * *